US012617792B2

(12) United States Patent
Zhang et al.

(10) Patent No.: US 12,617,792 B2
(45) Date of Patent: May 5, 2026

(54) PURINE DERIVATIVE, INTERMEDIATE AND APPLICATION THEREOF IN PREPARING ANTICANCER MEDICINE

(71) Applicant: SUZHOU RAYMON PHARMACEUTICALS COMPANY, LTD., Suzhou (CN)

(72) Inventors: Fei Zhang, Suzhou (CN); Zixia Feng, Suzhou (CN)

(73) Assignee: Suzhou Raymon Pharmaceuticals Company, Ltd., Suzhou (CN)

(*) Notice: Subject to any disclaimer, the term of this patent is extended or adjusted under 35 U.S.C. 154(b) by 826 days.

(21) Appl. No.: 17/754,934

(22) PCT Filed: Oct. 21, 2020

(86) PCT No.: PCT/CN2020/122436
§ 371 (c)(1),
(2) Date: Apr. 15, 2022

(87) PCT Pub. No.: WO2021/074814
PCT Pub. Date: Apr. 29, 2021

(65) Prior Publication Data

US 2022/0389017 A1 Dec. 8, 2022

(30) Foreign Application Priority Data

Oct. 24, 2019 (CN) ......................... 201911014796.5

(51) Int. Cl.
*C07D 473/34* (2006.01)
*A61P 35/00* (2006.01)

(52) U.S. Cl.
CPC ............ *C07D 473/34* (2013.01); *A61P 35/00* (2018.01); *C07B 2200/13* (2013.01)

(58) Field of Classification Search
CPC .... A61P 35/00; C07D 473/34; C07B 2200/13
See application file for complete search history.

(56) References Cited

U.S. PATENT DOCUMENTS

| | | | | |
|---|---|---|---|---|
| 11,242,346 B2 * | 2/2022 | Guo | ........................ | A61P 35/00 |
| 12,054,488 B2 * | 8/2024 | Zhang | ..................... | A61P 35/00 |

FOREIGN PATENT DOCUMENTS

| | | | | | |
|---|---|---|---|---|---|
| CN | 101730697 | A | | 6/2010 | |
| CN | 102711766 | A | | 10/2012 | |
| CN | 102712642 | A | | 10/2012 | |
| CN | 104230952 | A | | 12/2014 | |
| CN | 108794478 | A | * | 11/2018 | ........... C07D 473/34 |
| WO | WO 2010/120987 | A1 | | 10/2010 | |
| WO | WO 2010/120994 | A3 | | 10/2010 | |

OTHER PUBLICATIONS

Verheijen et al. Journal of medicinal chemistry 52, No. 24 (2009): 8010-8024 (Year: 2009).*
Gilbert et al. Bioorganic & medicinal chemistry letters 20, No. 2 (2010): 636-639 (Year: 2010).*
Nugiel et al. The Journal of Organic Chemistry 62, No. 1 (1997): 201-203 (Year: 1997).*
CN108794478A, English Machine Translation (Year: 2017).*
Braga, Dario, Simone d'Agostino, Elena Dichiarante, Lucia Maini, and Fabrizia Grepioni. "Dealing with crystal forms (the kingdom of serendip?)." Chemistry, An Asian Journal 6, No. 9 (2011): 2214-2223 (Year: 2011).*
International Search Report and Written Opinion issued for International Patent Application No. PCT/CN2020/122436, dated Dec. 31, 2020 in 15 pages including English translation.

* cited by examiner

*Primary Examiner* — James H Alstrum-Acevedo
*Assistant Examiner* — Carolyn L. Ladd
(74) *Attorney, Agent, or Firm* — Knobbe, Martens, Olson & Bear, LLP

(57) ABSTRACT

The present invention disclosures a novel purine derivatives represented by formula (I) or a pharmaceutically acceptable salt thereof, intermediate and application thereof inpreparation of a medicament for treating or preventing a cancer. This compound is a novel PI3K inhibitor with an excellent inhibitory activity, and may be useful for treating a variety of malignant tumors.

13 Claims, 1 Drawing Sheet

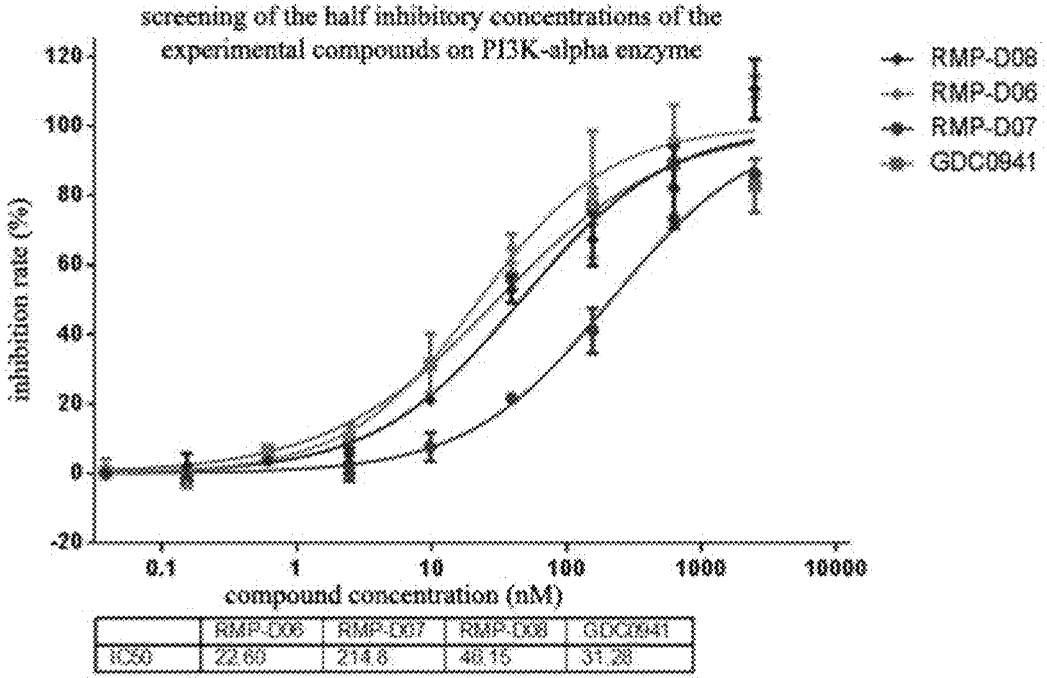
| | RMP-D06 | RMP-D07 | RMP-D08 | GDC0941 |
|---|---|---|---|---|
| IC50 | 22.60 | 214.8 | 48.15 | 31.28 |

PURINE DERIVATIVE, INTERMEDIATE AND APPLICATION THEREOF IN PREPARING ANTICANCER MEDICINE

CROSS-REFERENCE TO RELATED APPLICATIONS

This application is the U.S. National Phase under 35. U.S.C. § 371 of International Application PCT/CN2020/122436, filed Oct. 21, 2020, which claims priority to Chinese Patent Application No. 201911014796.5, filed Oct. 24, 2019. The disclosures of the above-described applications are hereby incorporated by reference in their entirety.

TECHNICAL FIELD OF THE INVENTION

The present disclosure belongs to the field of medicinal chemistry, and in particular relates to a class of novel purine derivatives and intermediates thereof, the novel purine derivatives have phosphatidylinositol-3-kinase (PI3K) inhibitory activity and can be used to prepare medicines for preventing and treating tumors.

BACKGROUND OF THE INVENTION

PI3K is an intracellular phosphatidylinositol kinase. Lewis C. Cantley, professor of cancer biomedicine at Weill Cornell Medical College, discovered the phosphatidylinositol-3-kinase (PI3K) signaling pathway and clarified its key role in tumor development. The PI3K signaling pathway is usually activated by receptors on the cell surface, such as receptors tyrosine kinases, GPCRs, and some oncogenes, such as RAS and the like. The activated p110 subunit catalyzes the conversion of PIP2 to PIP3 and activates Akt activity. Akt will further transmit signals to downstream molecules, such as mTORC1, GSK3, BCL-2 and the like to regulate different cellular physiological processes. mTORC2 activates the Akt molecules through phosphorylation of Ser at position 473. In contrast, PTEN can dephosphorylate PIP3 into PIP2. The downstream signaling pathways of PI3K molecules are more complex, including some feedback loops. Each of the four catalytic isomers of class I PI3K preferentially regulates specific signal transduction and tumor cell survival, depending on the type of malignant tumor and its genetic or epigenetic changes. For example, p110α is essential for the growth of tumor cells driven by PIK3CA mutations or oncogene RAS and receptor tyrosine kinases; p110β mediates the occurrence of PTEN-deficient tumors; and p110δ is highly expressed in white blood cells, thus making it has become an ideal target for the treatment of hematological malignancies.

In the late 1980s, PI3 kinase (PI3K) was discovered to be an enzyme that phosphorylates the 3-position of the inositol ring of phosphatidylinositol (D. Whitman et al. (1988) *Nature,* 332664). PI3K was originally thought to be a single enzyme, but it has now been clarified that there are multiple subtypes in PI3K, and PI3Kα is one of them. PI3Kα has high-frequency activating mutations in breast cancer, which is closely related to the development and drug resistance of breast cancer, and has become an important target for the treatment of breast cancer.

On Sep. 14, 2017, the U.S. FDA accelerated the approval of Bayer Healthcare Pharmaceuticals' Aliqopa® (Copanlisib), Aliqopa® is the trade name. It is used to treat patients suffering from recurrent follicular lymphoma.

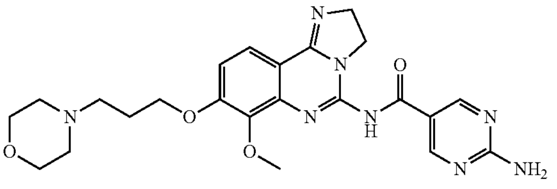

Copanlisib

Copanlisib is a phosphatidylinositol-3-kinase (PI3K) inhibitor, which has good inhibitory activity against the PI3K-α and PI3K-δ subtypes expressed in malignant B cells.

There are limited types of PI3Kα inhibitors and the efficacy of PI3Kα inhibitors in clinical trials varies greatly among individuals. It is desired to discover new PI3Kα inhibitors and biomarkers for efficacy prediction.

In the first half of 2019, the U.S. FDA announced that it has approved Piqray (alpelisib) developed by Novartis (NVS.US) to be used in combination with endocrine therapy fulvestrant to treat patients with HR+/HER2− advanced or metastatic breast cancer carrying PIK3CA gene mutations. These patients continue to get worse after receiving endocrine therapy. This is the first PI3K inhibitor approved by the FDA for the treatment of breast cancer. The tumors of patients with metastatic breast cancer have spread to other parts of the body, and the most common metastatic organs include bones, lungs, liver, and brain. In HR+/HER2− advanced breast cancer, changes in the PI3K pathway are the most common cause of tumor deterioration, disease progression, and drug resistance in treatment. About 40% of HR+/HER2− advanced breast cancer patients carry PIK3CA gene mutations. Pigmy is an oral small molecule α-specific PI3K inhibitor developed by Novartis, namely PI3Kα inhibitor. In breast cancer cell lines carrying PIK3CA gene mutations, it has shown the potential to inhibit the PI3K pathway and has the effect of inhibiting cell proliferation. The present disclosure also uses PI3Kα as the starting point for target research of new drugs, especially in China, there is no PI3Kα inhibitor invented in China for the treatment of malignant tumors. The structure of the innovative research of the present disclosure will fill this gap in China. Such as the final listing will have significant social and economic benefits.

SUMMARY OF THE INVENTION

The technical problem to be solved by the present disclosure is to provide a class of novel purine derivatives having PI3K inhibitory activity.

The present disclosure also provides an intermediate for preparing the above novel purine derivatives.

The present disclosure also provides an application of the above novel purine derivatives in preparing a medicine for preventing and/or treating phosphatidylinositol-3-kinase (PI3K)-mediated diseases.

In order to solve the above technical problems, the present disclosure adopts the following technical solution:

A purine derivative represented by Formula (I), or a stereoisomer, a pharmaceutically acceptable salt, a solvate or a crystal thereof (sometimes collectively referred to herein as "compounds of the present disclosure"):

(I)

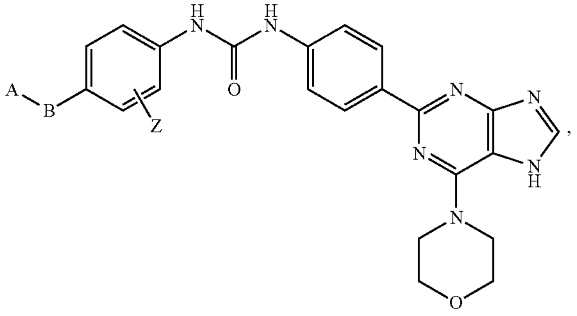

in the formula, A is selected from the group consisting of —OH, —$NH_2$, —SH,

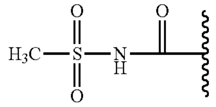
,
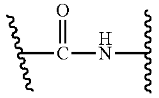
and
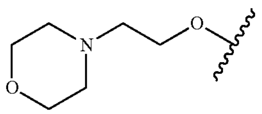
;

B is —$C_nH_{2n}$—, n is 1, 3 or 4; Z is selected from the group consisting of hydrogen, hydroxyl, $C_{1-3}$ alkyl, fluorine, chlorine and bromine, or is $C_{1-3}$ alkyl substituted by one or selected from fluorine, chlorine and bromine.

Further, Z is preferably selected from the group consisting of hydrogen, hydroxyl, fluorine, chlorine, bromine, methyl, ethyl, isopropyl, trifluoromethyl, and pentafluoroethyl, etc.

According to some preferred and specific aspects of the present disclosure, the structure of the purine derivative is represented by the following Formula (I-a).

(I-a)

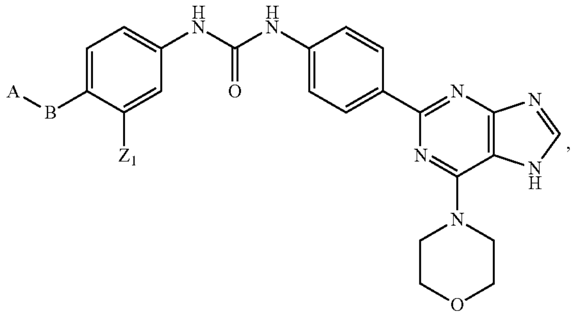

wherein, A, B and M are defined the same as above, and $Z_1$ is defined the same as Z. Further, $Z_1$ is selected from the group consisting of hydrogen, hydroxyl, fluorine, chlorine, bromine, methyl, ethyl, isopropyl, trifluoromethyl, and pentafluoroethyl, etc.

According to a further implementation of the present disclosure, B may be linear or branched, and there is no particular limitation.

According to some preferred aspects of the present disclosure, B is selected from the group consisting of —$CH_2$—, —$CH_2CH_2$—, —$CH_2CH_2CH_2$—, —$CH(CH_3)$—, —$CH(CH_3)CH_2$—, —$C(CH_3)_2$— and —$CH_2C(CH_3)_2$. Especially preferably, B is —$CH_2$—.

According to some preferred and specific aspects of the present disclosure, the purine derivative is selected from compounds represented by the following formulas:

I-1

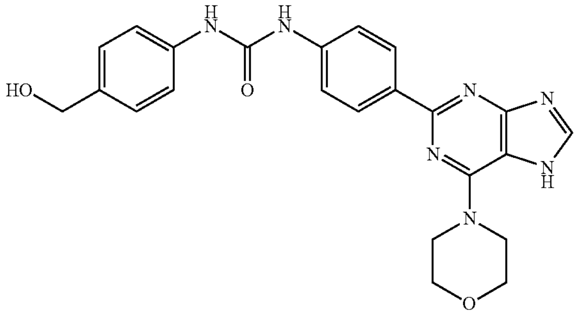

I-2

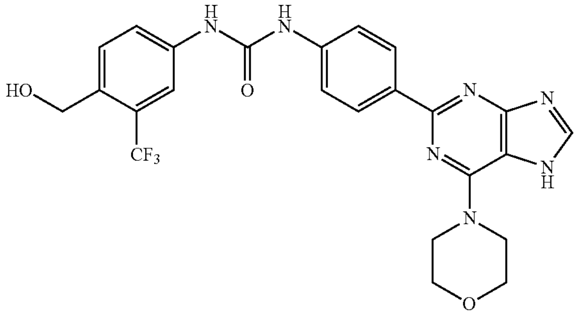

I-3

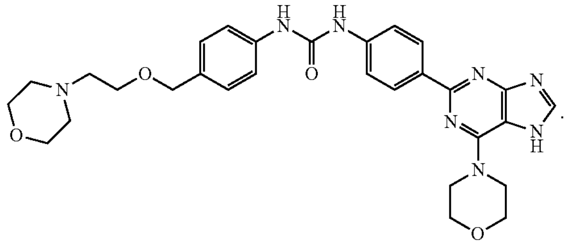

The present disclosure further provides a pharmaceutical composition containing one or more above-mentioned purine derivatives, or stereoisomers, pharmaceutically acceptable salts, solvates or crystals thereof. In some implemented examples, the composition further contains a pharmaceutical acceptable carrier.

The present disclosure provides an application of the purine derivative, or a stereoisomer, a pharmaceutically acceptable salt, a solvate or a crystal thereof, or a pharmaceutical composition containing the purine derivative in preparing a medicine for treating and/or preventing phosphatidylinositol-3-kinase (PI3K)-mediated diseases.

The phosphatidylinositol-3-kinase (PI3K)-mediated diseases generally comprise cancers. The cancers comprise, but are not be limited to, renal carcinoma, liver cancer, colon cancer, gastrointestinal stromal tumor, non-small cell lung cancer, breast cancer, pancreatic cancer, glioma, lymphoma, fibrosarcoma, ovarian cancer, leukemia and prostate cancer, etc.

The present disclosure further provides an application of the pharmaceutical composition in preparation of a medicine for treating and/or preventing cancer and a method for treating and/or preventing cancer using the pharmaceutical composition.

In the pharmaceutical composition according to the present disclosure, the compounds of the present disclosure are preferably present in a therapeutically effective amount.

The pharmaceutical acceptable carrier in the above pharmaceutical composition may be, for example, a pharmaceutically acceptable diluent, excipient, filler, binder, disintegrant, absorption enhancer, surfactant, lubricant, flavor, sweeteners, etc.

The medicine prepared by using the compounds of the present disclosure as active ingredients can be in various thrills such as tablets, powders, capsules, granules, oral in Formula (II), $A_1$ is tert-butyldimethylsiloxy (TBSO) or $A_1$ is the same as A in Formula (I);

B and Z are respectively the same as B and Z in Formula (I), and Y is an amino protection group.

According to some specific and preferred aspects of the present disclosure, the amino protection group is tetrahydro-2H-pyran-2-yl (THP).

According to some specific and preferred aspects of the present disclosure, the intermediate for preparing the above-mentioned novel purine derivative, or a stereoisomer, a pharmaceutically acceptable salt, a solvate or a crystal thereof, comprises the following compounds:

(II-1)

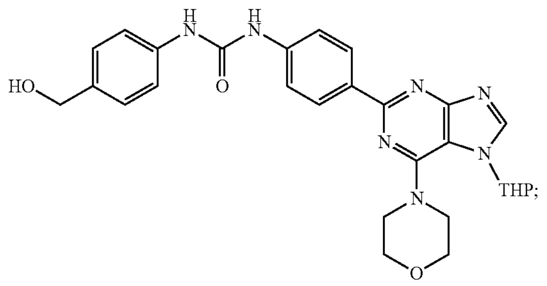

(II-2)

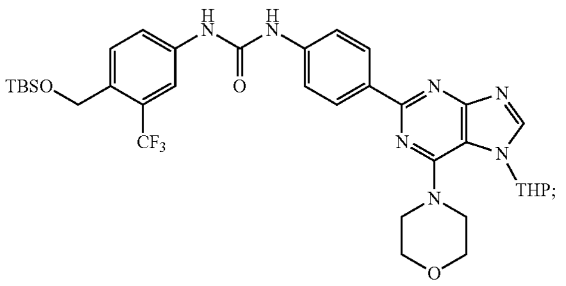

(II-3)

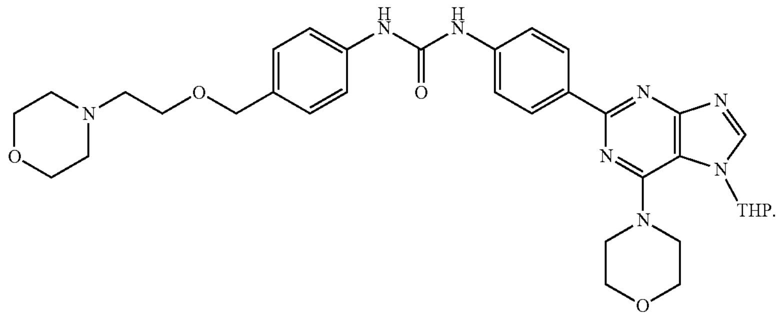

liquid, injection preparations and the like. The dosage form of the pharmaceutical composition is preferably a tablet, a capsule, or an injection.

The medicine in the above-mentioned various dosage forms can be prepared according to conventional methods in the field of pharmacy.

The present disclosure further provides an intermediate for preparing the purine derivative represented by Formula (I), or a stereoisomer, a pharmaceutically acceptable salt, a solvate or a crystal thereof and the intermediate has a structure represented by Formula (II):

(II)

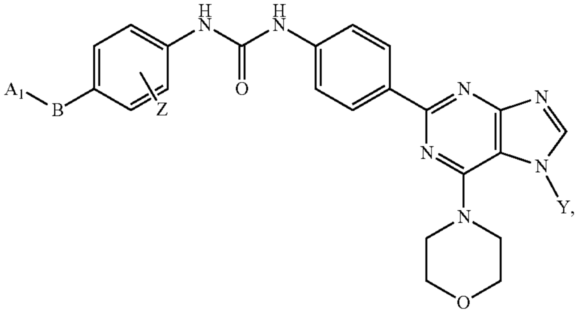

in some implementations of the present disclosure, the intermediate represented by Formula (II) may be prepared by reacting

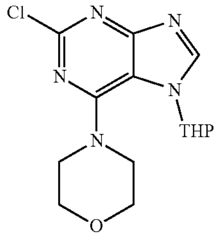

with a compound represented by Formula (III)

(III)

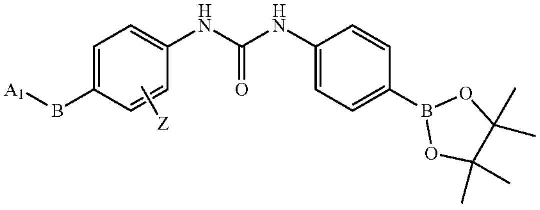

;

and in Formula (III), $A_1$, B and Z are defined the same as in Formula (II).

According to some preferred aspects of the present disclosure, in the process of preparing the intermediate represented by Formula (II), the reaction is carried out under an alkaline condition at a temperature of 30-120° C., and optionally under an inert atmosphere. More preferably, in the process of preparing the intermediate represented by Formula (II), the reaction is carried out at a temperature of 40-110° C., preferably at a temperature of 50-105° C., more preferably at a temperature of 60-100° C., and even more preferably at a temperature of 70-95° C. According to some specific aspects of the present disclosure, in the process of preparing the intermediate represented by Formula (II), the reaction is carried out at a temperature of 80-90° C.

According to some implementations of the present disclosure, the inert atmosphere is a nitrogen atmosphere.

According to some implementations of the present disclosure, the alkaline condition is formed by adding an alkaline substance, and the alkaline substance is selected from the group consisting of potassium acetate, potassium carbonate, potassium phenoxide, potassium phosphate, potassium tert-butoxide, sodium carbonate, sodium bicarbonate, sodium tert-butoxide, sodium methoxide, sodium ethoxide, triethylamine, tri-n-butylamine, diisopropylethylamine, and combinations thereof. According to a preferred and specific aspect of the present disclosure, the alkaline substance is sodium bicarbonate.

According to some preferred aspects of the present disclosure, in the process of preparing the intermediate represented by Formula (II), the reaction is carried out in the presence of 2-dicyclohexylphosphino-2,4,6-triisopropylbiphenyl and/or tris(dibenzylideneacetone)dipalladium. According to a specific and preferred aspect of the present disclosure, in the process of preparing the intermediate represented by Formula (II), the reaction is carried out in the co-presence of 2-dicyclohexylphosphino-2,4,6-triisopropylbiphenyl and tris(dibenzylideneacetone)dipalladium.

Due to the implementation of the above technical solutions, the present disclosure has the following advantages over the prior art:

The present disclosure provides a novel purine derivative, which has excellent PI3K inhibitory activity, and can be applied to treat phosphoinositide-3-kinase (PI3K)-mediated diseases, and provide more and better medicine choices for cancer treatment. In addition, compared with existing PI3K inhibitors, the purine derivative of the present disclosure has a simple structure and a relatively low preparation cost.

BRIEF DESCRIPTION OF THE DRAWINGS

FIG. 1 shows the relationship curves of the inhibition rates of Compound I-1 to Compound I-3 and the positive control compound GDC-0941 on PI3Kα.

DETAILED DESCRIPTION OF EXEMPLARY EMBODIMENTS

Definition of Terms

Unless otherwise defined, all technical and scientific terms used herein have the same meaning as commonly understood by one of ordinary skill in the art to which this disclosure belongs.

The term "isomer" refers to an isomer produced by the different arrangement of atoms in a molecule in space, and includes cis-trans isomers, enantiomers and conformational isomers. All stereoisomers are within the scope of the present disclosure. The compounds of the present disclosure may be a single stereoisomer or a mixture of other isomers such as a racemate, or a mixture of all other stereoisomers.

The term "salt" refers to a pharmaceutically acceptable salt formed by a compound of the present disclosure with an acid, the acid may be an organic or inorganic acid, specifically selected from the group consisting of phosphoric acid, sulfuric acid, hydrochloric acid, hydrobromic acid, citric acid, maleic acid, malonic acid, mandelic acid, succinic acid, fumaric acid, acetic acid, lactic acid, nitric acid, sulfonic acid, p-toluenesulfonic acid, malic acid, methanesulfonic acid or analogues thereof.

The term "solvate" refers to a form of a compound of the present disclosure that forms a solid or liquid complex by coordination with a solvent molecule. Hydrates are a special form of solvates in which coordination occurs with water. Within the scope of the present disclosure, the solvate is preferably a hydrate.

The term "crystal" refers to the various solid forms formed by the compounds described herein, including crystalline forms and amorphous forms.

The following embodiments may enable those skilled in the art to fully understand the present disclosure, but do not limit the present disclosure in any way. The structures of all compounds were confirmed by $^1H$ NMR or MS.

The compounds used in the embodiments are abbreviated as follows:

DBU: 1,8-diazabicyclo[5.4.0]undec-7-ene;
DMF: N,N-dimethylformamide;
THF: tetrahydrofuran;
$Pd(dppf)Cl_2$: [1,1'-bis(diphenylphosphino)ferrocene]dichloropalladium;
DTT: dithiothreitol;
ATP: adenosine triphosphate;
TK: tyrosine kinase;
HEPES: 2-[4-(2-hydroxyethyl)-1-piperazinyl]ethanesulfonic acid.

Embodiment 1: Preparation of Compound 14

Compound I-1 was synthesized through the following route:

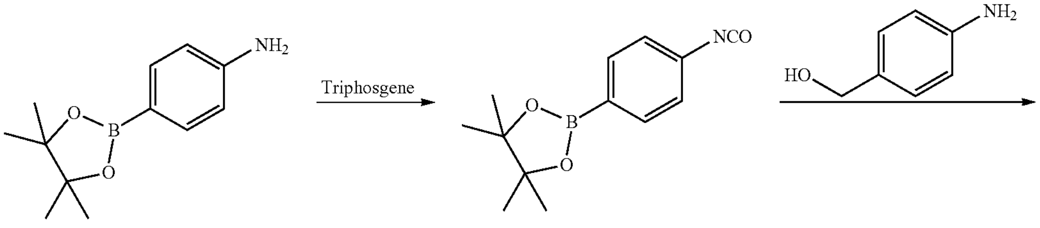

1 2

-continued
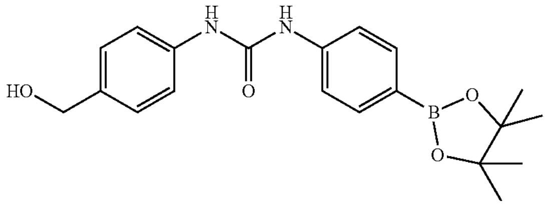
3
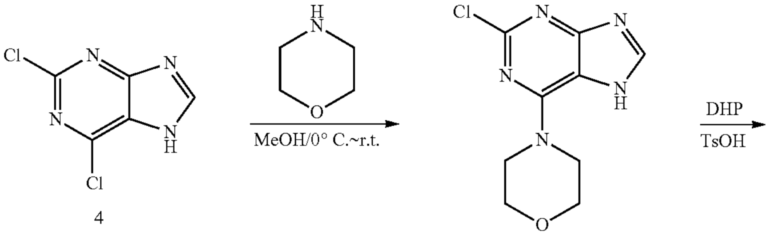
4
5
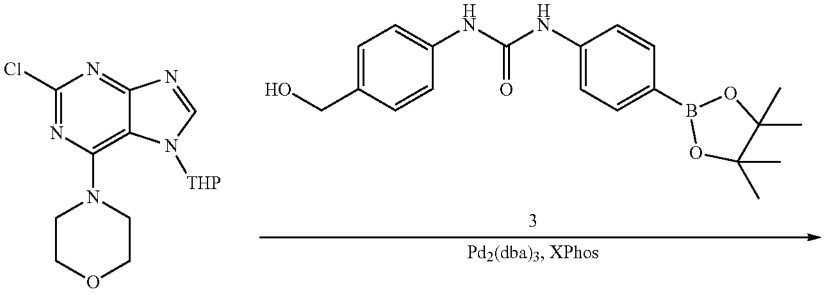
6
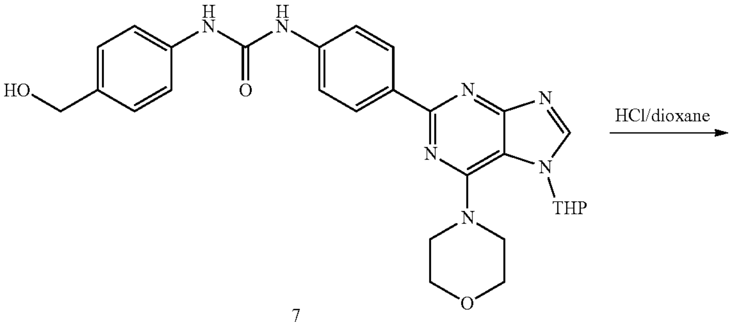
7
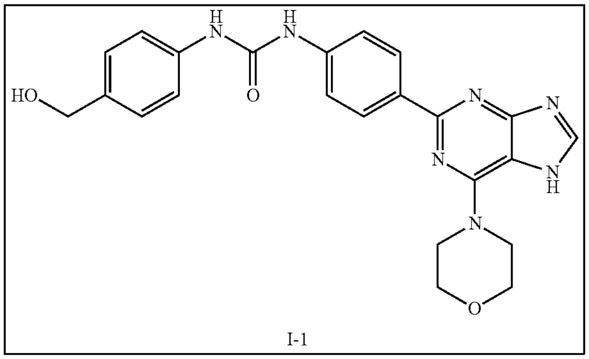
I-1

1.1. Synthesis of Compound 2

Compound 2

2-(4-isocyanatophenyl)-4,4,5,5-tetramethyl-1,3,2-dioxaborolane

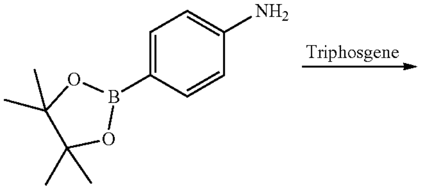

1

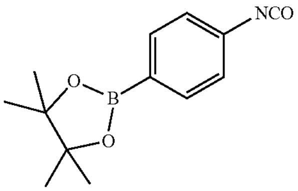

2

Compound 1, namely 4-aminophenylboronic acid pinacol ester (10 g, 45.6 mmol), and triethylamine (13.8 g, 136.8 mmol) were added into 300 mL of dichloromethane, cooled to zero ° C., triphosgene (8.1 g, 27.4 mmol) was slowly added at zero ° C. in batches and then stirred at zero ° C. for 50 minutes to give a solution of Compound 2, which was used directly in the next step.

1.2. Synthesis of Compound 3

Compound 3

1-(4-(hydroxymethyl)phenyl)-3-(4-(4,4,5,5-tetramethyl-1,3,2-dioxaborolan-2-yl)phenyl)urea

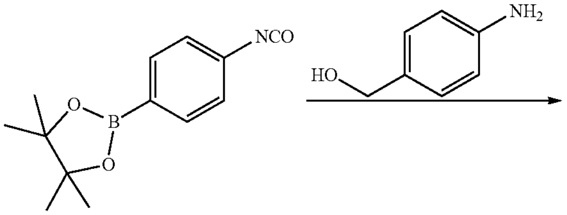

2

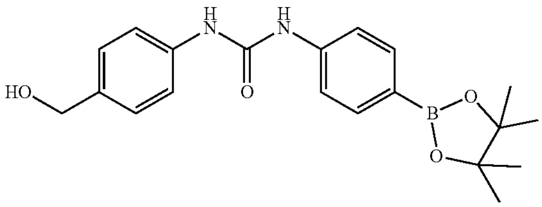

3

P-aminobenzyl alcohol (8.4 g, 68 mmol) was added to the above-mentioned solution of Compound 2 at zero degree Celsius, then the system was stirred at zero degree Celsius for 15 minutes, warmed to room temperature, and stirred at room temperature for another 3 hours. LC-MS detection showed the reaction completion, the reaction solution was concentrated and spin-dried, and extracted with dichloromethane, and the organic phase was washed with sodium bicarbonate solution and saturated sodium chloride solution, dried over anhydrous sodium sulfate, and filtered, and the filtrate was spin-dried, and purified by column chromatography (dichloromethane/methanol=40:1) to give yellow solid, namely Compound 3 (11 g, yield=60%). Measured: ESI-MS m/z=369 $[M+1]^+$. $^1H$ NMR (DMSO-d6, 400 MHz): δ 9.02 (s, 1H), 8.89 (s, 1H), 7.60-7.58 (d/J=8 Hz, 2H), 7.49-7.47 (d, J=8.4 Hz, 2H), 7.42-7.40 (d, J=8 Hz, 2H), 7.24-7.21 (d, J=8.4 Hz, 2H), 5.06 (m, 1H), 4.44-4.42 (d, J=5.6 Hz, 2H), 1.28 (s, 12H).

1.3. Synthesis of Compound 5

Compound 5: 4-(2-chloro-7H-purin-6-yl)morpholine

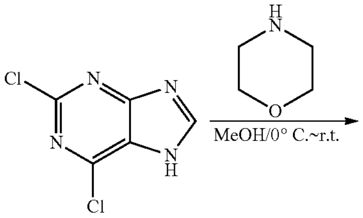

4

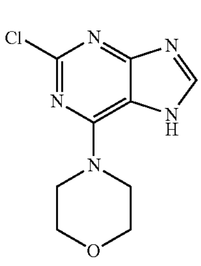

5

2,6-dichloropurine (18.9 g, 0.1 mol, Compound 4) was dissolved in methanol (400 mL) and cooled to zero degree Celsius, morpholine (13 mL, 0.15 mol) was slowly added dropwise in the range of 0 to 5 degrees Celsius, then stirred at zero degree Celsius for 15 minutes, warmed to room temperature, and stirred at room temperature for another 3 hours. LC-MS detection showed the reaction completion, a large amount of yellow solid was precipitated and filtered, and the filter cake was washed with 20 mL of methanol, 50 mL of water and 50 mL of ethyl ether to give off-white solid, namely Compound 5 (21.1 g, yield=88%). Measured: ESI-MS m/z=240 $[M+1]^+$. $^1H$ NMR (DMSO-d6, 400 MHz): δ 11.23 (s, 1H), 8.16 (s, 1H), 4.19 (m, 4H), 3.74-3.71 (m, 4H).

1.4. Synthesis of Compound 6

Compound 6

4-(2-chloro-7-(tetrahydro-2H-pyran-2-yl)-7H-purin-6-yl)morpholine

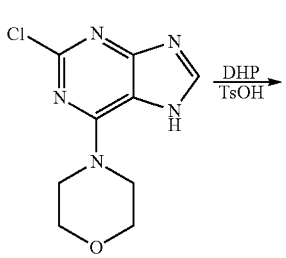

5

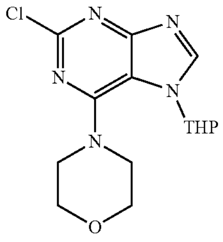

6

Compound 5 (16.0 g, 0.067 mol) was suspended in ethyl acetate (480 mL), and 3,4-dihydro-2H-pyran (8.4 g, 0.1 mol, DHP) and monohydrate 4-methylbenzenesulfonic acid (1.0 g, 5.2 mmol, TsOH) were added at room temperature. The reaction mixture was stirred at 75 degrees Celsius overnight to give a black solution. The reaction mixture was cooled to room temperature, washed with saturated sodium bicarbonate aqueous solution, then the organic phase was dried over anhydrous sodium sulfate, and filtered. The filtrate was vacuum concentrated to dry methyl tertiary-butyl ether (20 mL) and petroleum ether (50 mL) were added to the residual, and the system was stirred for 0.5 h and filtered, and the filter cake was vacuum dried to give Compound 6 (20.0 g, yield=92.6%). Measured: ESI-MS m/z=324 $[M+1]^+$. $^1H$ NMR ($CDCl_3$, 400 MHz): δ 7.91 (s, 1H), 5.72-5.69 (m, 1H), 4.29-3.73 (m, 10H), 2.10-2.02 (m, 2H), 1.91-1.65 (m, 4H).

1.5. Synthesis of Compound 7

Compound 7

1-(4-(hydroxymethyl)phenyl)-3-(4-(6-morpholino-7-tetrahydro-2H-pyran-2-yl)-7H-purin-2-yl)phenyl) urea

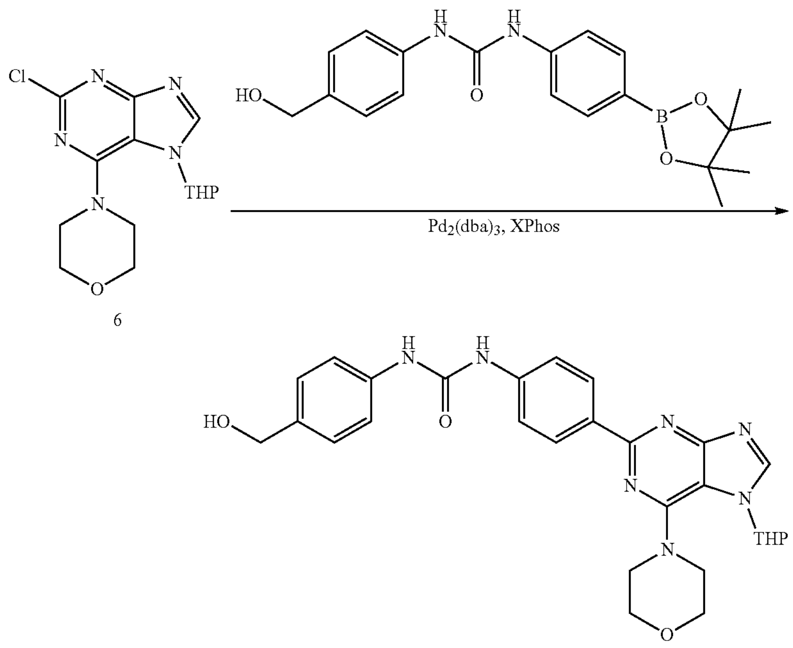

6

7

Compound 6 (2.0 g, 6.2 mmol) was dissolved in 1,4-dioxane (25 mL) and water (3 mL), and then Compound 3 (2.3 g, 6.2 mmol), sodium bicarbonate (1.7 g, 20.4 mmol), XPhos (400 mg, 2-dicyclohexylphosphino-2,4,6-triisopropylbiphenyl) and $Pd_2(dba)_3$ (180 mg, tris(dibenzylideneacetone)dipalladium) were added, then the system was replaced with nitrogen for 3 times. The system was stirred at 85 degrees Celsius for 2 days under nitrogen atmosphere. The reaction solution was vacuum concentrated, then water (20 mL) was added, and the reaction solution was extracted with ethyl aceteate (50 mL*2), the organic phases were dried over anhydrous sodium sulfate and filtered, and the filtrate was vacuum concentrated to dry. Methyl tertiary-butyl ether (30 mL) was added, and the system was stirred at morn temperature for 0.5 h and filtered, and the filter cake was vacuum dried to give offwhite solid Compound 7 (1.3 g, yield>39.6%). Measured: ESI-MS m/z=530$[M+1]^+$.

1.6. Synthesis of Compound I-1

Compound I-1

1-(4-(hydroxymethyl)phenyl)-3-(4-(6-morpholino-7H-purin-2-yl)phenyl)urea

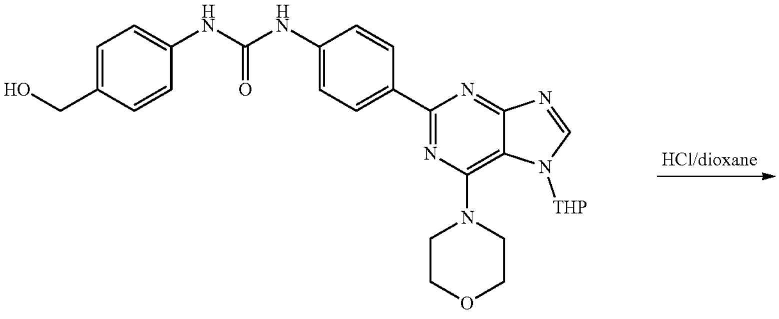

7

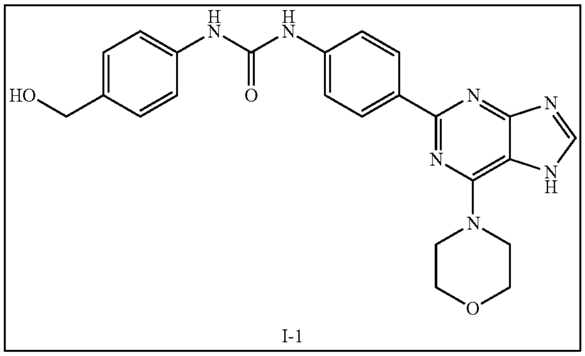

I-1

Compound 7 (1.4 g, 10.6 mmol) was suspended in 1,4-dioxane (5 mL), a solution of hydrogen chloride in dioxane (4N, 15 mL) was added, the system was stirred at room temperature overnight. The reaction was complete as determined by LCMS. The system was filtered, and the filter cake was washed with dioxane, and vacuum dried to give yellow solid Compound I-1 (1.0 g, yield>21%). Measured: $^1H$ NMR (DMSO-d6, 400 MHz): δ 8.36 (s, 1H), 8.24-8.22 (m, 2H), 7.64-7.62 (d, J=8.8 Hz, 2H), 7.50-7.37 (m, 3H), 7.27-7.25 (d, J=8.4 Hz, 1H), 4.72 (s, 1H), 4.45 (s, 1H), 4.28 (m, 4H) 3.82 (m, 4H). LCMS [mobile phase: from 95% water (0.1% TFA) and 5% $CH_3CN$ to 5% water (0.1% TFA) and 95% $CH_3CN$ in 6.5 min, finally under these conditions for 0.5 min.] purity is >90%, Rt=3.699 min; MS Calcd.: 445; MS Found: 446 $[M+H]^+$.

Embodiment 2: Preparation of Compound I-2

Compound I-2 was synthesized through the following route:

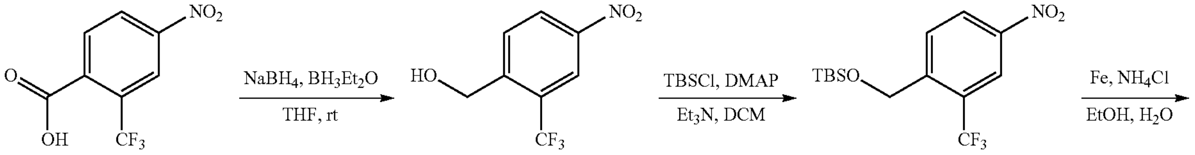

8 9 10

-continued
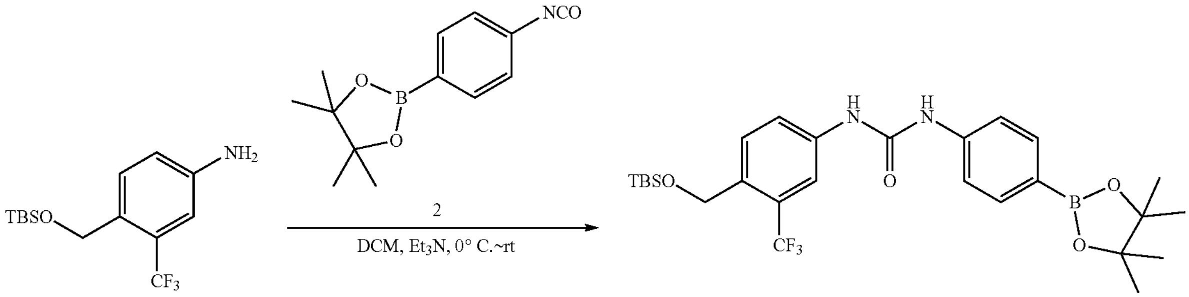
11
12
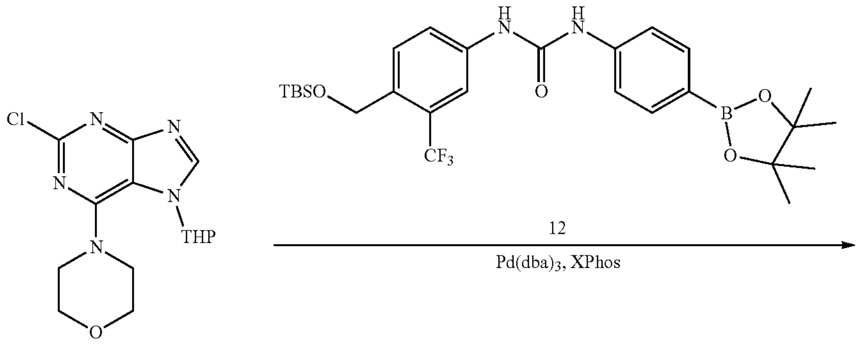
6
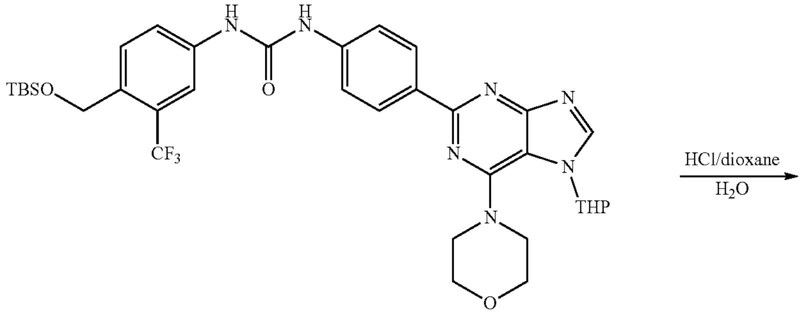
13
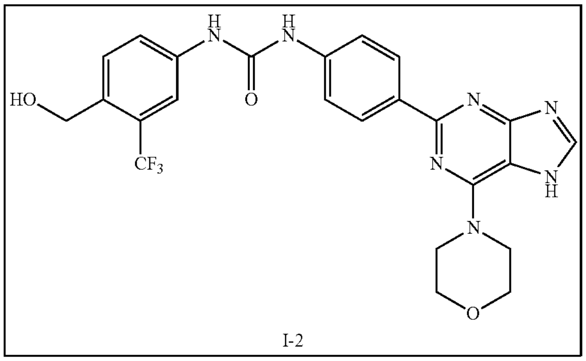
I-2

2.1. Synthesis of Compound 9

Compound 9: (4-nitro-2-(trifluoromethyl)phenyl)methanol

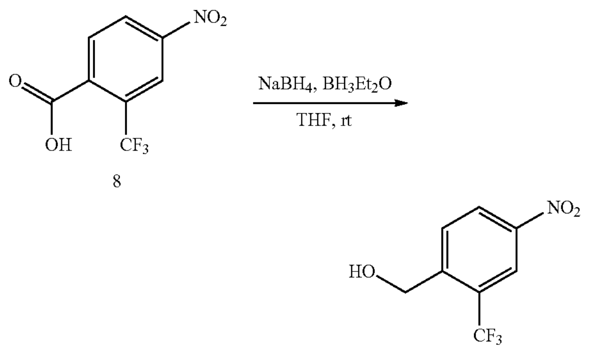

8

9

Compound 8 (25.0 g, 106.4 mmol) was dissolved in tetrahydrofuran (100 mL), sodium borohydride (11.5 g, 319.1 mmol) was slowly added in an ice bath, and boron trifluoride diethyl etherate (20 mL) was slowly added drop-wise, and stirred at room temperature overnight. After TLC detection showed the reaction completion, 100 mL of brine was added, and the system was extracted with ethyl acetate (300 mL×3), and the organic phases were dried over sodium sulfate and concentrated to give Compound 9 (14.5 g, yield=61%). Measured: ESI-MS m/z=222 $[M+1]^+$.

2.2. Synthesis of Compound 10

Compound 10 tert-butyldimethyl((4-nitro-2-(trifluoromethyl)benzyl)oxy)silane

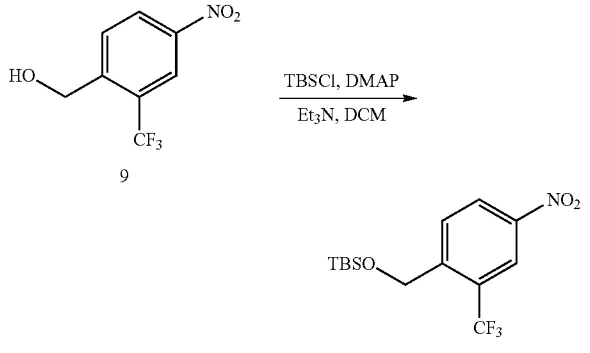

9

10

Compound 9 (14.0 g, 63.6.4 mmol), tert-butyldimethyl-silyl chloride (19.2 g, 127.27 mmol), triethylamine (16.1 g, 159.1 mmol) and p-dimethylaminopyridine (0.78 g, 6.36 mmol) were added to dichloromethane (120 mL) in ice bath, and then the reaction solution was stirred at room temperature for 2 h. After TLC detection showed the reaction completion, 100 mL of brine: was added, and the system was extracted with dichloromethane (200 mL×3), and the organic phases were concentrated by drying with sodium sulfate and purified by column chromatography (petroleum ether/ethyl acetate=100:1-50:1) to give Compound 10 (15.0 g, yield=70%), which was directly used in the next step.

2.3. Synthesis of Compound 11

Compound 11

4-(((tert-butyl dimethylsilyl)oxy)methyl)-3-(trifluoromethyl)aniline

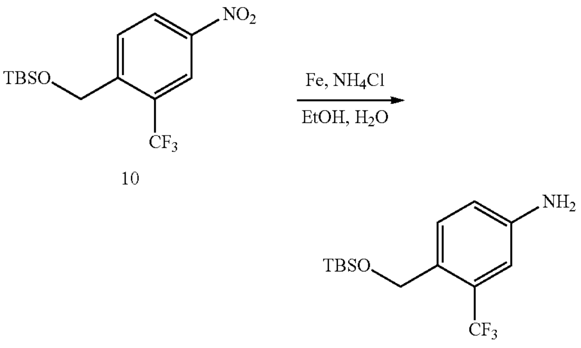

10

11

Compound 10 (15.0 g, 44.78 mmol) was dissolved in ethanol/water (200 mL/80 mL), ammonium chloride (15.0 g, 268.68 mmol) was added, and the system was warmed to a temperature of 80° C., then iron powder (11.0 g, 201.49 mmol) la was added, the reaction was carried out at this temperature for 1 h. After LCMS detection showed the reaction completion, brine (100 mL) was added, and the system was extracted with ethyl acetate (200 mL×3), and the organic phases were dried over sodium sulfate and concentrated to give Compound 11 (11.0 g, yield=80%). Measured: ESI-MS m/z=306 $[M+1]^+$. $^1H$ NMR ($CDCl_3$, 400 MHz): δ 7.49 (d, J=8.0 Hz, 1H), 6.90 (s, 1H), 6.83 (d, J=8.0 Hz, 1H), 4.78 (s, 2H), 0.94 (s, 9H), 0.09 (s, 6H).

2.4. Synthesis of Compound 12

Compound 12

1-(4-(((tert-butyldimethylsilyl)oxy)methyl)-3-(trifluoromethyl)phenyl)-3-(4-(4,4,5,5-tetramethyl-1,3,2-dioxaborolan-2-yl)phenyl)urea

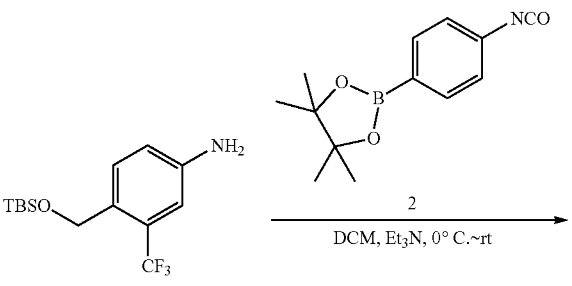

11

-continued

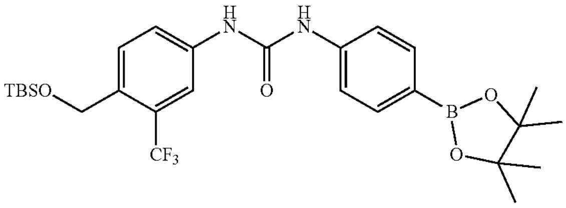

12

Compound 11 (6.0 g, 19.68 mol) was dissolved in tetrahydrofuran (90 mL), and then Compound 8 (12.0 g, 49.19 mmol) was added. The system reacted at room temperature overnight. After LCMS detection showed the reaction completion, the reaction solution was vacuum concentrated, and purified by column chromatography (petroleum ether/ethyl acetate=10:1-5:1) to give Compound 12 (5.5 g, yield=50%). Measured: ESI-MS m/z=551.6[M+1]$^+$.

2.5. Synthesis of Compound 13

Compound 13

1-(4-(((tert-butyldimethylsilyl)oxy)methyl)-3-(trifluoromethyl)phenyl)-3-(4-(6-mor pholino-7-(tetrahydro-2H-pyran-2-yl)-7H-purin-2-yl)phenyl)urea

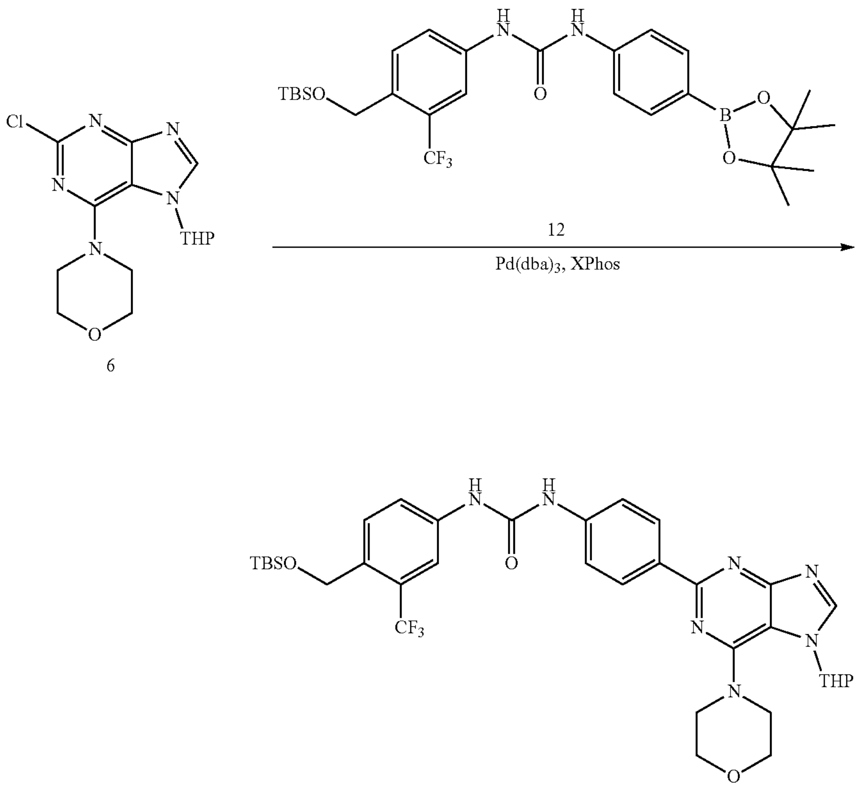

6

13

Compound 12 (5.5 g, 10.0 mmol) was dissolved in 1,4-dioxane (80 mL)/water (5 mL), then Compound 6 (3.6 g, 11.00 mmol), sodium bicarbonate (2.6 g, 30.0 mmol), XPhos (476 mg, 1.0 mmol) and $Pd_2(dba)_3$ (184 mg, 0.20 mmol) were added. The reaction was carried out at 85° C.: overnight. After LCMS detection showed the reaction completion, 35 mL of brine was added, and the system was extracted with ethyl acetate (100 mL×3), the organic phase was dried over sodium sulfate, concentrated, and purified by column chromatography (petroleum ether/ethyl acetate=5:1-1:1) to give a crude product, which was purified by reverse column to give Compound 13 (2.0 g, yield=28%). Measured: ESI-MS m/z=712.9[M+1]$^+$. $^1$H NMR ($CDCl_3$, 400 MHz): δ 8.40-8.38 (m, 2H), 7.95 (s, 1H), 7.69-7.67 (m, 1H), 7.60-7.57 (m, 2H), 7.41 (d, J=8.4 Hz, 2H), 7.08 (s, 1H), 7.00 (s, 1H), 5.86-5.82 (m, 1H), 4.83 (s, 2H), 4.35 (brs, 4H), 4.19-4.16 (m, 1H), 3.87-3.78 (m, 5H), 2.16-1.99 (m, 3H), 1.84-1.73 (m, 3H), 0.93 (s, 9H), 0.09 (s, 6H).

2.6. Synthesis of Compound I-2

Compound I-2

1-(4-(hydroxymethyl)-3-(trifluoromethyl)phenyl)-3-(4-(6-morpholino-7H-purin-2-yl)phenyl)urea

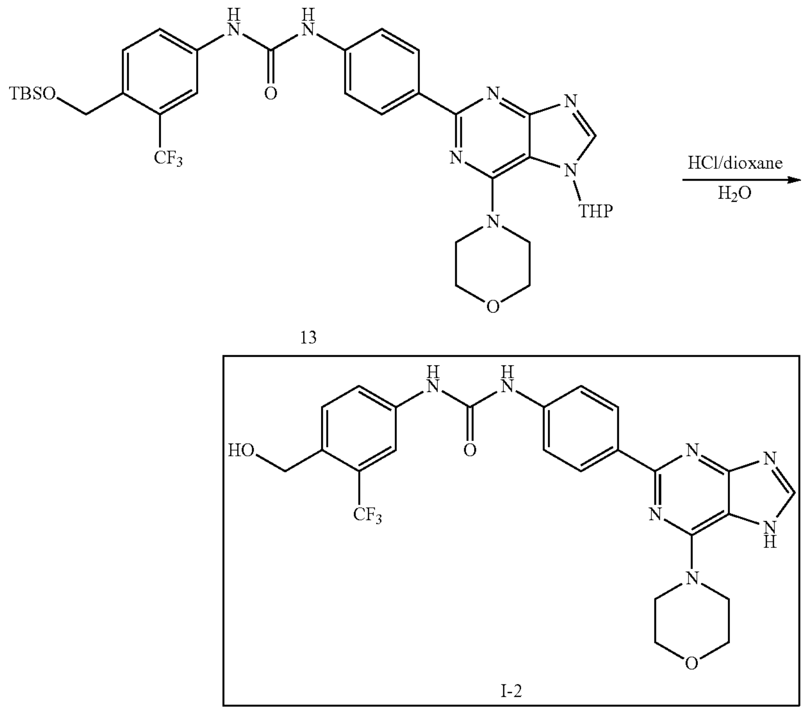

13

I-2

Compound 13 (2.0 g, 2.81 mmol) was dissolved in 1,4-dioxane (8 mL), and then water (30 mL) and 1 M of a solution of hydrochloride acid in dioxan (80 mL) were added. The system was stirred at room temperature overnight, and after LCMS detection showed the reaction completion, the system was filtered. The obtained insolubles were respectively slurried with water, acetonitrile, and methyl tert-butyl ether, and dried to give Compound I-2 (1.3 g, yield 92%). Measured: $^1$H NMR (DMSO-d6, 400 MHz): δ 9.50-9.44 (m, 2H), 8.29-8.27 (m, 3H), 7.97 (s, 1H), 7.68-7.59 (m, 4H), 4.61 (s, 2H), 4.29 (brs, 4H), 3.80-3.78 (m, 4H). $^1$H NMR (DMSO-d6+$D_2O$, 400 MHz): δ 9.36-9.32 (m, 0.3H), 8.29-8.26 (m, 3H), 7.97 (s, 1H), 7.68-7.60 (m, 4H), 4.61 (s, 2H), 4.29 (brs, 4H), 3.80-3.78 (m, 4H), LCMS [mobile phase: from 95% water (0.02% $NH_4Ac$) and 5% $CH_3CN$ to 5% water (0.02% $NH_4Ac$) and 95% $CH_3CN$ in 6.5 min, finally under these conditions for 0.5 min.] purity is >97%, Rt=3.485 min; MS Calcd.: 513; MS Found: 514 $[M+H]^+$.

Embodiment 3: Preparation of Compound I-3

Compound I-3 was synthesized through the following route

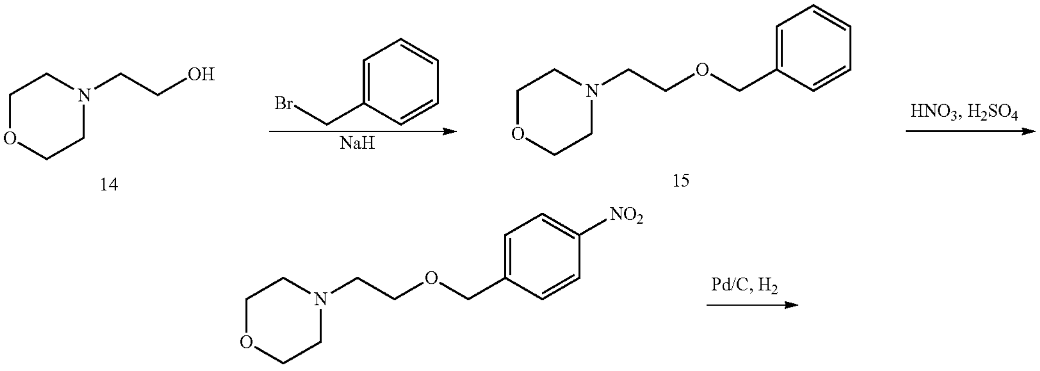

14

15

16

-continued
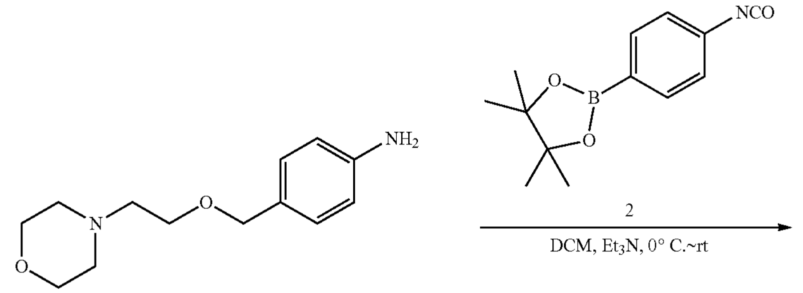
17
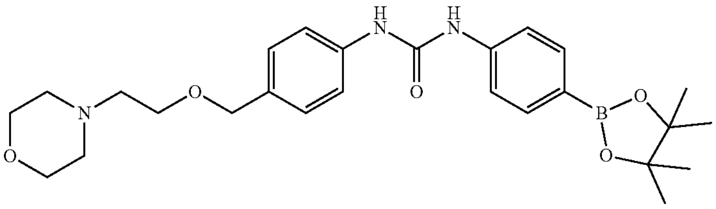
18
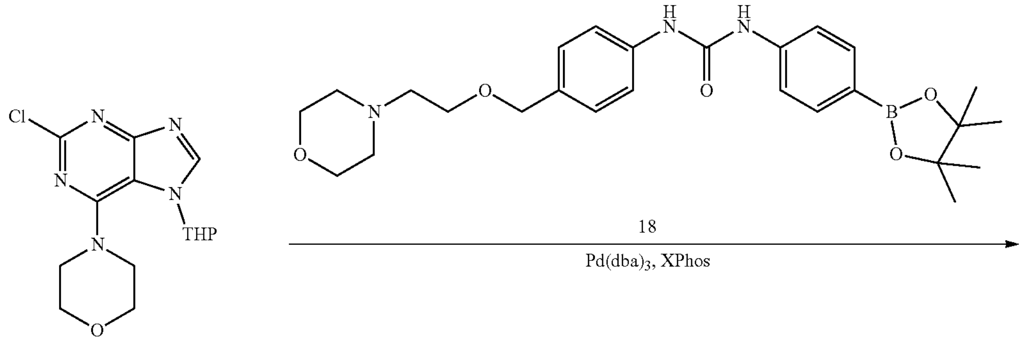
6
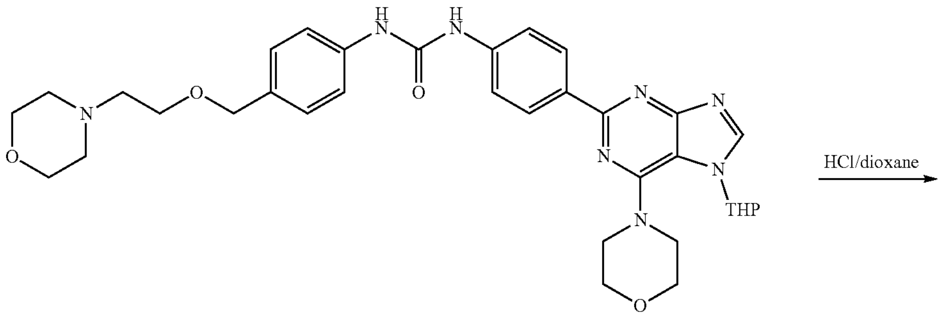
19
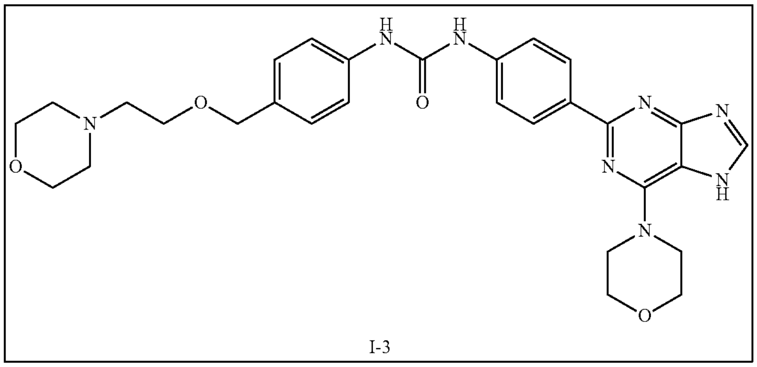
I-3

3.1. Synthesis of Compound 15

Compound 15: 4-(2-(benzyloxy)ethyl)morpholine

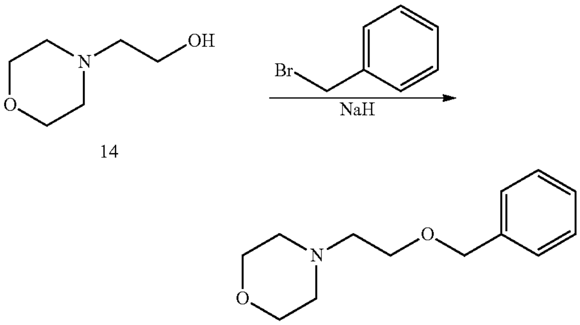

14

15

Compound 14 (32.8 g, 0.25 mol) was dissolved in DMF (200 mL), NaH (10 g, 0.25 mol) was added in batches in an ice-water bath, and the system was stirred at room temperature for 1.5 hours, and then benzyl bromide (39.3 g, 0.23 mol) was added dropwise. The reaction solution was stirred at room temperature for 16 hours, vacuum concentrated, then ethyl acetate (100 mL) was added and the reaction solution was washed with water and saturated brine. The organic phase was vacuum concentrated, and purified by silica gel column (DCM:MeOH=10:1) to give colorless oil, namely Compound 15 (40 g, yield 78%). Measured: ESI-MS m/z=222 $[M+1]^+$.

3.2. Synthesis of Compound 16

Compound 16: 4-(2-((4-nitrobenzyl)oxy)ethyl)morpholine

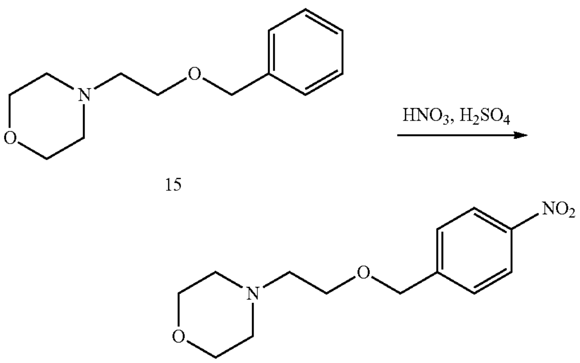

15

16

Compound 15 (40.0 g, 0.18 mol) was dissolved in acetic anhydride (200 mL), cooled to 5° C. in an ice-water bath, fuming nitric acid (60 ml) was added dropwise, and stirred at 5° C. for 4 hours. The reaction solution was slowly poured into aqueous sodium carbonate solution to make pH>8, and extracted with ethyl acetate. The organic phase was washed with water and saturated brine, vacuum concentrated, and purified by silica gel column (DCM:MeOH=10:1) to give colorless oil, namely Compound 16 (30.1 g, yield 62%). Measured: ESI-MS m/z=267 $[M+1]^+$.

3.3. Synthesis of Compound 17

Compound 17: 4-((2-morpholinoethoxy)methyl)aniline

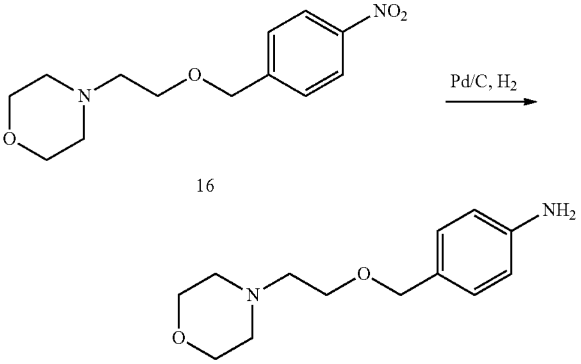

16

17

Compound 16 (5.0 g, 0.018 mol) was dissolved in ethyl acetate (200 mL), 10% palladium on carbon (1.0 g) were added, and the system was replaced with hydrogen for 3 times, and stirred at room temperature for 16 hours under hydrogen atmosphere. The reaction solution was filtered, and the filtrate was vacuum concentrated to dryness to give a red crude, namely Compound 17 (4.5 g), which was directly used in the next step. Measured: ESI-MS m/z=237 $[M+1]^+$.

3.4. Synthesis of Compound 18

Compound 18

1-(4-((2-morpholinoethoxy)methyl)phenyl)-3-(4-(4,4,5,5-tetramethyl-1,3,2-dioxaborolan-2-yl)phenyl)urea

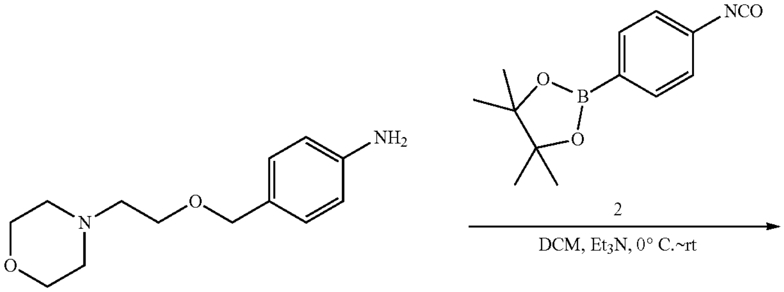

2

17

-continued

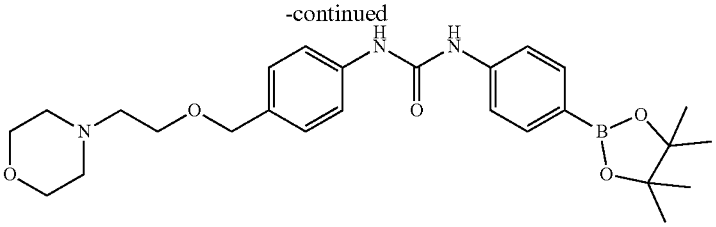

18

To a dichloromethane solution of Compound 2 (100 mL, from 6.6 g of Compound 1, 30 mmol) was added dropwise a dichloromethane solution (30 mL) of Compound 17 (5.9 g, 25 mmol) in an ice bath. The reaction solution was stirred overnight at room temperature, washed with aqueous sodium bicarbonate solution, washed with water, and the organic phase was vacuum concentrated, and purified by silica gel column (DCM:MeOH=10:1) to give yellow solid, namely Compound 18 (8.7 g, yield 72.3%). Measured: ESI-MS m/z=482[M+1]$^{+}$.

3.5. Synthesis of Compound 19

Compound 19

1-(4-(6-morpholino-7-(tetrahydro-2H-pyran-2-yl)-7H-purin-2-yl)phenyl)-3-(4-((2-morpholinoethoxy)methyl)phenyl)urea Compound 18 (3.8 g, 8.28 mmol) was dissolved in 1,4-dioxane (80 mL)/water (8 mL), then Compound 6 (3.0 g, 9.29 mmol), sodium bicarbonate (2.1 g, 24.84 mmol), XPhos (395 mg) and $Pd_2(dba)_3$ (152 mg) were added. The reaction was carried out at 85° C. overnight. After LCMS detection showed the reaction completion, 20 mL, of brine was added, and the system was extracted with ethyl acetate, the organic phase was dried over sodium sulfate, concentrated, and purified by silica gel column (dichloromethane/methanol=30:1-10:1), and then purified by a reverse column to give Compound 19 (1.5 g, yield=29%). Measured: ESI-MS m/z=643.8 [M+1]$^{+}$. $^{1}$H NMR (DMSO-d6, 400 MHz): δ 8.89 (s, 1H), 8.72 (s, 1H), 8.35-8.33 (m, 3H), 7.57 (d, J=8.8 Hz, 2H), 7.45 (d, J=8.0, 2H), 7.24 (d, J=8.0 Hz, 2H), 5.80-5.75 (m, 1H), 4.39 (s, 2H), 4.30 (brs, 3H), 4.06-4.03 (m, 1H), 3.78-3.71 (m, 5H), 3.56-3.49 (m, 6H), 3.36-3.35 (m, 1H), 2.51-2.47 (m, 2H), 2.39 (brs, 4H), 2.31-2.22 (m, 1H), 1.99-1.97 (m, 2H), 1.79-1.76 (m, 1H), 1.64-1.60 (m, 2H).

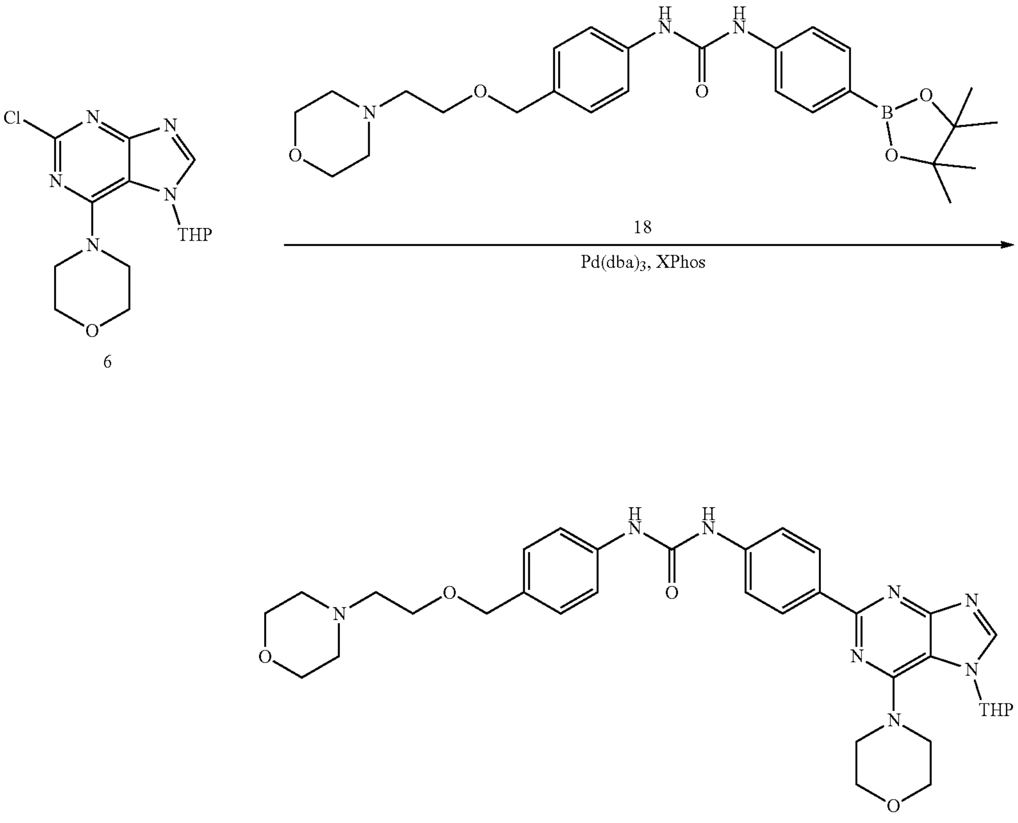

19

3.6. Synthesis of Compound I-3

Compound I-3

1-(4-(6-morpholino-7H-purin-2-yl)phenyl)-3-(4-((2-morpholinoethoxy)methyl)phenyl)urea

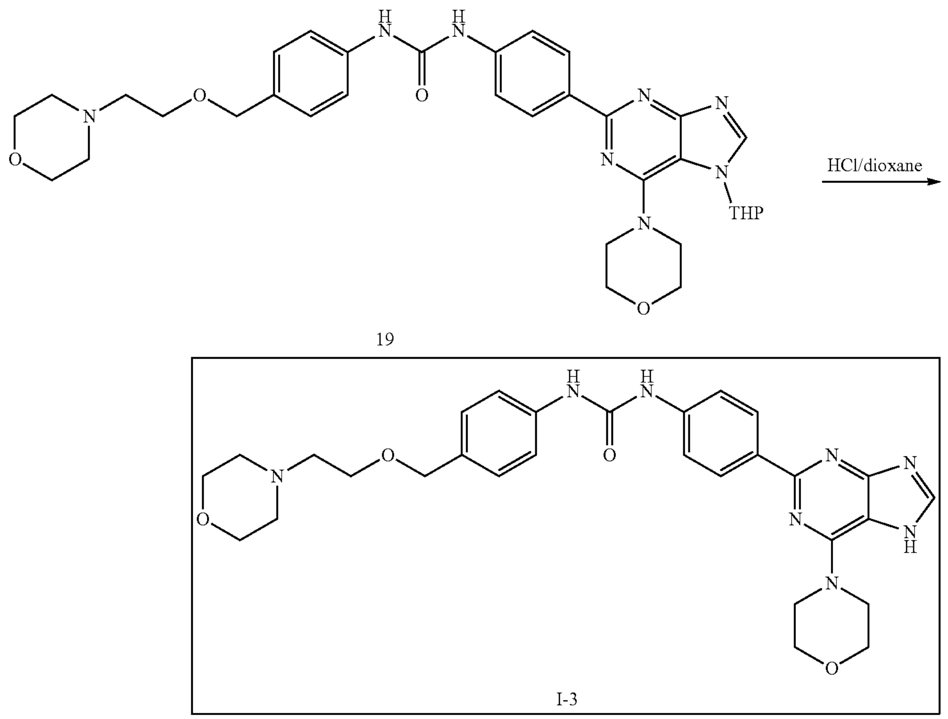

19

I-3

Compound 19 (2.5 g, 3.89 mmol) was dissolved in a 0.3 Ni solution (60 mL) of hydrochloric acid in 1,4-dioxane, and then water (5 mL) was added. The system was stirred at room temperature for 2 h, and after LCMS detection showed the reaction completion, the system was filtered. The obtained insolubles were respectively slurried with acetonitrile, ethyl acetate and methyl Cert-butyl ether, and dried to give Compound I-3 (2.0 g, yield 91%). Measured: $^1$H NMR (DMSO-d6, 400 MHz): δ 10.99 (s, 1H), 9.92 (s, 1H), 9.69 (s, 1H), 8.40 (s, 1H), 8.28 (d, J=8.4 Hz, 2H), 7.63 (d, J=9.2 Hz, 2H), 7.49 (d, J=8.4 Hz, 2H), 7.29 (d, J=8.41 Hz, 2H), 4.47 (s, 2H), 4.29 (brs, 4H), 3.96-3.93 (m, 2H), 3.85-3.79 (m, 8H), 3.42-3.34 (m, 4H), 3.16-3.09 (m, 2H). $^1$H NMR (DMSO-d6+$D_2O$, 400 MHz): δ 8.38-8.37 (m, 1H), 8.25 (d, J=8.4 Hz, 2H), 7.63 (d, J=8.4 Hz, 2H), 7.49 (d, J=7.2 Hz, 2H), 7.31 (d, J=8.4 Hz, 2H), 4.49 (s, 2H), 4.29 (brs, 4H), 3.81-3.75 (m, 10H), 3.43-3.35 (m, 4H), 3.17-3.11 (m, 2H). LCMS [mobile phase: from 95% water (0.02% $NH_4Ac$) and 5% acetonitrile to 5% water (0.02% $NIH_4Ac$) and 95% acetonitrile in 6.5 min, finally under these conditions for 1 min.] purity is >97%, Rt=3.258 min; MS Calcd.: 558; MS Found: 559 ([M+1]$^+$).

Embodiment 4: Biological Activity Experiment of the Compounds of the Embodiments PI3-Kinase (human) HTRF™ Assay kit (PI3-Kinase (human) HTRF™ Assay kit detection method is an international general method) was used to detect the half inhibitory concentration of PI3K alpha enzyme (IC50 determination)) of the 3 compounds, namely Compound I-1, Compound I-2, Compound I-3 (in the following experiments, they were respectively given code RMP-D06, RMP-D07, RMP-D08) in the embodiments, and the compound GDC-0941 was used as a positive control. Positive control substance: GDC0941 (Pictilisib) with the following structural formula:

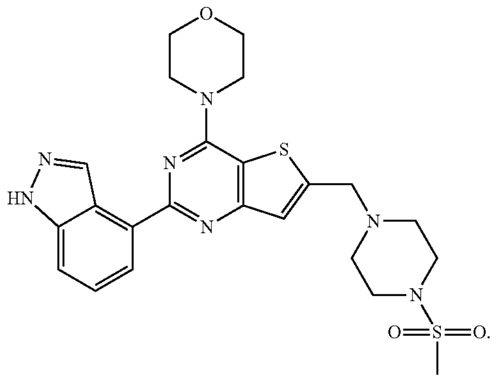

GDC0941 (Pictilisib)

7.1 Materials and Instruments

2104 EnVision® Multilabel Reader (Cat: 2104-0010, PerkinElmer);

384 well opaque balck plate (Cat. 6007270, PerkinElmer);

PI3-Kinase (human) HTRF™ Assay kit (Cat. 33-016, Millipore);

4× Reaction Buffer (Cat. 33-002, Millipore); PIP2 1 mM (Cat. 33-004, Millipore); Stop A (Cat, 33-306, Millipore); Stop B (Cat. 33-008, Millipore); DM A (Cat. 33-010, Millipore); DM B (Cat. 33-012, Millipore); DM C (Cat. 33-014, Millipore); PI3k alpha (Cat. 14-602, Millipore); ATP 10 mM (cat PV3227, Invitrogen); DTT 1M (cat D5545, Sigma);

Compounds to be tested: Compound I-1, Compound I-2, Compound I-3 (in the following experiments, they were respectively given codes RMP-D06, RMP-D07, RMP-D08), and GDC-0941.

7.2 Reagent Preparation

1× Reaction Buffer

4× Reaction Buffer was diluted to 1× with $ddH_2O$, and 1M DTT was added to make the final concentration of 5 mM. Prepare fresh before each use. For example, to prepare 10 mL 1× Reaction Buffer, adding 2.5 mL 4× Reaction Buffer, 50 μL 1 M DTT, and 7.45 mL $ddH_2O$, Throughout the experiment, freshly prepared 1× Reaction Buffer was used to prepare ATP working solution, substrate and enzyme mixed working solution, etc.

4× Compound Working Solution

The compound to be tested was dissolved in DMSO to 1 mM as a storage solution, and then diluted with DMSO in a 4-fold ratio for a total of 10 concentration points. 1 μL of each was added to 24 μL 1× Reaction Buffer. 5 μL of each diluted solution was added into a 384-well plate and contained 1% DMSO.

2×PIP2 Working Solution

1× reaction buffer was used to prepare 2×PIP2 working solution to make the final concentration of 20 μM and PIP2 reaction final concentration of 10 μM, for example, to prepare 1 ml 1× reaction buffer/PIP2 working solution, add 20 μL of PIP2 to 980 μL 1× reaction buffer. This working solution should be prepared with 0.1-0.2 ml more to meet the control usage and dead volume.

2×PIP2/Kinase Working Solution

The kinase was diluted with 2×PIP2 working solution, and the concentration of the kinase working solution was 10 ng/well.

Kinase-Free Control (it can be Regarded as 100% Inhibition)

That is, 2×PIP2 working solution.

4×ATP Working Solution 10 mM ATP was diluted to 40 μM with 1× reaction buffer. In a 20 μL kinase reaction system, the concentration of ATP was 10 μM. For example, to prepare 2 ml ATP working solution, take 8 μL 10 mM ATP and add it to 1992 μL 1× reaction buffer.

Stop Solution

Stop A and Stop B were mixed in a ratio of 3:1 and can be used after at least 2 hours at room temperature. The stop solution can be stable for 12 hours at room temperature.

Test Solution

DMC, DMA and DMB were mixed in a ratio of 18:1:1, and can be used after at least 2 hours at room temperature. The test solution can be stable for 12 hours at room temperature.

7.3 Experimental Procedure

| | Reagent | Screening group Kinase + compound | Control group 100% inhibition Kinase-free | Control group 0% inhibition With kinase and no compound |
|---|---|---|---|---|
| Kinase response | 4× Compound | 5 μL | — | — |
| | 4% DMSO | — | 5 μL | 5 μL |
| | 2× PIP2 | — | 10 μL | — |
| | 2× PIP2/kinase | 10 μL | — | 10 μL |
| | 4× ATP | 5 μL | 5 μL | 5 μL |
| | After mixing, incubate at room temperature for 30 min | | | |
| Test | Stop Solution | 5 μL | 5 μL | 5 μL |
| | Test Solution | 5 μL | 5 μL | 5 μL |
| | After mixing, incubate at room temperature for 2 hours | | | |
| Excitation at 320 nM, and emission signal detection at 665 nm, 620 nm | | | | |

Data Analysis

Calculation of the Emission Ratio (ER) of Each Well

Emission Ratio (ER)=665 nM Emission signal/620 nm Emission signal

The average emission intensity ratio (Emission Ratio) of the 100% inhibition control is recorded as: $ER_{100\%}$ The average Emission Ratio of the 0% inhibition control is recorded as: $ER_{0\%}$ Calculation of the Inhibition Rate The inhibition rate is calculated with the following formula:

$$\text{Inhibition rate}=(ER_{sample}-ER_{0\%})/(ER_{100\%}-ER_{0\%})\times 100\%[(\text{ERpositive}-\text{ERsample})/(\text{ERpositive}-\text{ERnegative})*100\%]$$

7.4 Experimental Results

PI3-Kinase (human) HTRF™ Assay kit was used to detect the inhibition rate of the 3 compounds on PI3K-alpha enzyme at different concentrations, with the concentration of DMSO controlled to 1%, double holes for each concentration, and selecting GDC-0941 as a positive reference substance. The measurement results are shown in FIG. 1. According to the test results, the half inhibitory concentration ($IC_{50}$) of each compound on PI3K-alpha enzyme is summarized in Table 1 below.

TABLE 1 the half inhibitory concentrations ($IC_{50}$) of the tested compounds on PI3K-alpha

| Compound | $IC_{50}$ (nM) |
|---|---|
| RMP-D06 | 22.6 |
| RMP-D07 | 214.8 |
| RMP-D08 | 46.15 |
| GDC0941 | 31.28 |

The above experiments proved the inhibitory effect of the novel purine derivative of the present disclosure on phosphatidylinositol-3-kinase (PI3K), indicating that the novel purine derivative (including its pharmaceutically acceptable salts, etc.) of the present disclosure is a kind of new PI3K inhibitor. Therefore, it can be used to treat phosphatidylinositol-3-kinase-mediated diseases, and its treatable malignancies include but are not limited to renal carcinoma, liver cancer, colon cancer, gastrointestinal stromal tumor, non-small cell lung cancer, breast cancer, pancreatic cancer, glioma, lymphoma, fibrosarcoma, ovarian cancer, leukemia and prostate cancer, etc.

The other compounds of the present disclosure have basically the same structure as Compound I-1 to Compound I-3, and it can be expected that they have excellent activities comparable to Compound I-1 to Compound I-3. This class of compounds is the world's first new type of compound, which has shown obvious strong activity, and will be used in further new drug research to invent domestically-made innovative drugs, to use in cheap anti-cancer drugs with strong effects and small side effects urgently needed in the market.

The explanation on the above embodiments is only to help understanding of the method and its core concept of the present disclosure. It should be noted that, for those ordinary skilled in the art, various improvements and modifications can be made without depart from the technical principle of the present disclosure, and these improvements and modifications should be covered by the protective scope of the present disclosure.

What is claimed is:

1. The purine derivative represented by Formula (I-1), or a stereoisomer or a pharmaceutically acceptable salt thereof,

I-1

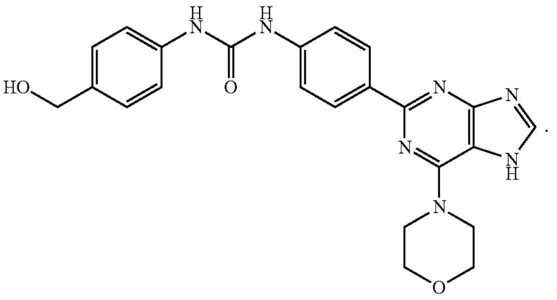

2. A method for preparing a medicine comprising: preparing the purine derivative represented by Formula (I-1), or a stereoisomer or a pharmaceutically acceptable salt thereof according to claim 1.

3. A pharmaceutical composition, wherein the pharmaceutical composition comprises:

the purine derivative represented by Formula (I-1), or a stereoisomer or a pharmaceutically acceptable salt thereof according to claim 1; and a pharmaceutical acceptable carrier.

4. The pharmaceutical composition according to claim 3, wherein the pharmaceutical composition is a pharmaceutical composition.

5. An intermediate for preparing a purine derivative represented by Formula (I-1)), or a stereoisomer or a pharmaceutically acceptable salt thereof according to claim 1, wherein the intermediate has a structure represented by Formula (II-1):

(II-1)

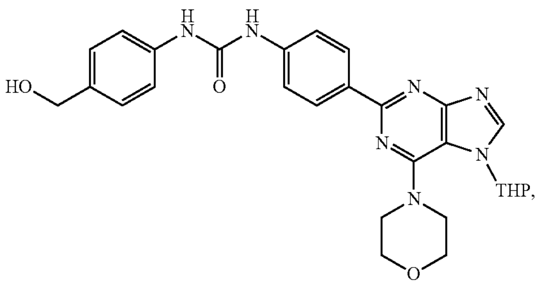

wherein THP is tetrahydro-2H-pyran-2-yl.

6. A method for preparing the intermediate according to claim 5, wherein the intermediate is prepared by reacting

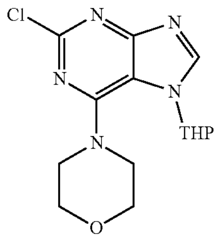

with a compound represented by Formula (III)

(III)

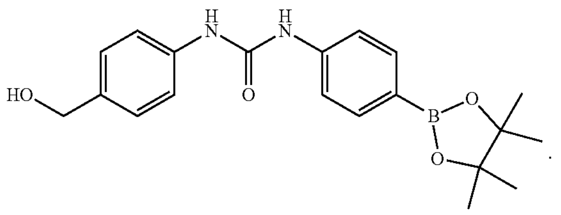

7. The method according to claim 6, wherein, in the process of preparing the intermediate represented by Formula (II-1), the reaction is carried out under an alkaline condition at a temperature of 30-120° C., or under an inert atmosphere.

8. The method according to claim 7, wherein, in the process of preparing the intermediate represented by Formula (II-1), the reaction is carried out at a temperature of 40-110° C.

9. The method according to claim 8, wherein, in the process of preparing the intermediate represented by Formula (II-1), the reaction is carried out at a temperature of 80-90° C.

10. The method according to claim 7, wherein the alkaline condition is formed by adding an alkaline substance selected from the group consisting of potassium acetate, potassium carbonate, potassium phenoxide, potassium phosphate, potassium tert-butoxide, sodium carbonate, sodium bicarbonate, sodium tert-butoxide, sodium methoxide, sodium ethoxide, triethylamine, tri-n-butylamine, diisopropylethylamine, and combinations thereof.

11. The method according to claim 6, wherein, in the process of preparing the intermediate represented by Formula (II-1), the reaction is carried out in the presence of 2-dicyclohexylphosphino-2,4,6-triisopropylbiphenyl, and/or tris(dibenzylideneacetone) dipalladium.

12. The method according to claim 11, wherein, in the process of preparing the intermediate represented by Formula (II-1), the reaction is carried out in the co-presence of 2-dicyclohexylphosphino-2,4,6-triisopropylbiphenyl and tris(dibenzylideneacetone) dipalladium.

13. The method according to claim 7, wherein, in the process of preparing the intermediate represented by Formula (II-1), the reaction is carried out at a temperature of 50-105° C.

* * * * *